United States Patent [19]

Shimamoto et al.

[11] Patent Number: 5,250,433
[45] Date of Patent: Oct. 5, 1993

[54] GRAMINEOUS HYBRID PLANTS AND PROCESS FOR PREPARING THEM

[75] Inventors: Ko Shimamoto, Kanagawa; Junko Watanabe, Tokyo; Rie Terada; Yasuyuki Hayashi, both of Kanagawa, all of Japan

[73] Assignees: Mitsubishi Kasei Corporation; Mitsubishi Corporation, both of Tokyo, Japan

[21] Appl. No.: 770,766

[22] Filed: Oct. 5, 1991

Related U.S. Application Data

[63] Continuation of Ser. No. 474,668, Feb. 6, 1990, abandoned, which is a continuation of Ser. No. 97,163, Sep. 16, 1987, abandoned.

[30] Foreign Application Priority Data

Sep. 20, 1986 [JP] Japan ................. 223346

[51] Int. Cl.$^5$ .......................... A01H 4/00; C12N 5/26
[52] U.S. Cl. .......................... 435/240.47; 435/172.2; 800/220; 800/DIG. 57; 935/94; 935/98
[58] Field of Search ................. 800/220, DIG. 55, 57; 435/172.2, 240.47, 240.51, 240.54; 935/94, 98

[56] References Cited

U.S. PATENT DOCUMENTS 4,677,066 6/1987 Takahashi et al. ............... 435/172.2

FOREIGN PATENT DOCUMENTS 114529 8/1984 European Pat. Off. .
0202667 11/1986 European Pat. Off. ....... 435/240.47

OTHER PUBLICATIONS

Evans, DA in DA Evans et al., eds., Handbook of Plant Cell Culture, vol. 1, Macmillan Publ. Co., N.Y., pp. 297–298 and 304 (1983).
Gamborg et al. (1981) in TA Thorpe, ed., Plant Tissue Culture, Academic Press, N.Y., pp. 115–153.
Yamada et al. (1984) in Ammuato et al., eds., Handbook of Plant Cell Culture, vol. 3, Macmillan Publ. Co., N.Y., pp. 164–165.
Auw et al. (1984) in IK Vasil, ed. Cell Culture and Somatic Cell Genetics of Plants, vol. 1, Academic Press, Inc., N.Y., pp. 199–203.
L. Menczel (1984) in IK Vasil, ed., as above, pp. 428–432.
DW Galbraith 91984) in IK Vasil, ed., as above, pp. 433–435 and 441–442.
T. Kameya (1984) in IK Vasil, ed., as above, pp. 423–427.
Poehlman, J. M. (1959) Breeding Field Crops, Henry Holt and Co., Inc., N.Y., p. 183.
Menezel (1984) in Vasil, ed., as above, pp. 428–432.
Galbraith (1984) in Vasil, ed., as above, pp. 433–435 and 441–442.
Zimmermann, et al. (1981) Planta 151(1): 26–32.
Li et al. (1988) Acta Genet Sin 15(5): 321–328.
Evans in Evans et al., eds, Handbook of Plant Cell Culture, vol. 1, Macmillan Publishing Co., N.Y., pp. 297–298, 1983.
Aviv et al. (1984) in Vasil, ed. Cell Culture and Somatic Cell Genetics of Plants, vol. 1, Academic Press, Inc., N.Y., pp. 199–203.
Terada, et al. (1987) Mol. Gen. Genet. 210: 39–43.
Hayashi, et al. (1988) Mol. Gen. Genet. 214: 6–10.
Kyozuka, et al. (1987) Mol. Gen. Genet. 206: 408–413.
Plant & Cell Physiol. vol. 20, No. 7, 1979 pp. 1441–1443; M. Senda et al. "Induction of cell fusion of plant protoplasts by electrical stimulation".
Mol. Gen. Genet. (1987), 210: 39–43, R. Terada et al.

*Primary Examiner*—Che S. Chereskin
*Attorney, Agent, or Firm*—Oblon, Spivak, McClelland, Maier & Neustadt

[57] ABSTRACT

According to the present invention, there is provided a gramineous hybrid plant produced from a rice-derived protoplast and another gramineous plant-derived protoplast. Also provided by the invention is an efficient process for preparing such a gramineous hybrid plant wherein a protoplast is prepared from a callus or suspension cell of a rice plant (*Oryza sativa*), another protoplast is separately prepared from a callus or suspension cell of another gramineous plant, these protoplasts are subjected to cell fusion by electric treatment, the thus fused cells are cultivated in a culture medium containing cultured rice cells as nurse cells, and the thus formed colonies are then cultivated in a culture medium containing a plant hormone such as 2,4-dichlorophenoxyacetic acid.

6 Claims, 1 Drawing Sheet

GRAMINEOUS HYBRID PLANTS AND PROCESS FOR PREPARING THEM

This application is a continuation of application Ser. No. 07/474,668 filed on Feb. 6, 1990, which was a continuation of U.S. application Ser. No. 07/097,163, filed Sep. 16, 1987, now both abandoned.

BACKGROUND OF THE INVENTION

1. Field of the Invention

The present invention relates to hybrid plants in the Gramineae produced by the cell fusion method and to an efficient process for producing such plants.

2. Description of the Prior Art

The cell fusion method is an effective means for obtaining a hybrid between different species or genera, which cannot be obtained by conventional breeding methods.

With respect to gramineous plants including the cereals, however, there has been only one report on the cell fusion between pearl millet (*Pennisetum glaucum*) and guinea grass (*Panicum maximum*): see Mol. Gen. Genet., 203, 365–370 (1986). No other case of cell fusion between important crops has been reported.

In order to efficiently produce hybrid plants, conditions for cell fusion, and methods for screening hybrids and plant regeneration should be established. However, there have been few reports on such conditions and methods concerning plants in the Gramineae.

SUMMARY OF THE INVENTION

Therefore, it is an object of the present invention to provide a new gramineous plant produced by the cell fusion method, more particularly a somatic hybrid plant between rice (*Oryza sativa*) and another gramineous plant.

Another object of the invention is to provide an efficient process for producing such a hybrid plant in the Gramineae.

BRIEF DESCRIPTION OF THE DRAWING

The invention will be described in detail with reference to the attached drawing in which.

DETAILED DESCRIPTION OF THE INVENTION

Figure 1:
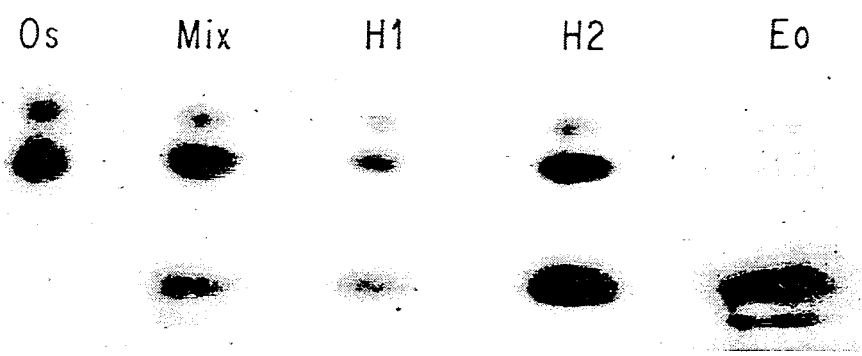
FIG. 1 is a picture showing the electrophoretic band pattern of LAP (leucine aminopeptidase) isozymes; Os corresponds to rice (*Oryza sativa*), Eo to *Echinocloa oryzicola*, $H_1$ and $H_2$ to hybrid calluses obtained according to the process of the invention, and Mix to a mixture of Os and Eo.

The above mentioned objects can be attained by the practice of the process according to the present invention, in which protoplasts prepared from callus or suspension cells derived from rice (*Oryza sativa*) and protoplasts prepared from callus or suspension cells derived from another Gramineae species are subjected to cell fusion, the resulting fused cells are cultured in a culture medium containing cultured cells of rice (*Oryza sativa*) as nurse cells to thereby form colonies, and the colonies are further cultured in a medium containing plant hormones.

Rice (*Oryza sativa*) plants which can be used in the practice of the invention may include many rice varieties such as NIHONBARE, KOSHIHIKARI, SASANISHIKI and the like.

Suspension cells or callus derived from mature or immature seeds, leaf sheaths or root tissues, or the like, of rice is cultivated in a liquid medium to prepare protoplasts.

More specifically, for instance, the above mentioned plant material may be sterilized by sodium hypochlorite or the like, placed on e.g. Murashige and Skoog (MS) agar culture medium (Physiol. Plant, 15, 473–497 (1962)), and then cultured at 25–28° C. under 2,000–3,000 lux (17 hr/day). The thus induced callus may then be subjected to shake culture at 50–150 rpm under the same temperature and light conditions as mentioned above in MS or R2 liquid culture medium (Plant Cell Physiol., 14, 1113–1121 (1973)).

In the preparation of protoplasts of another gramineous plant other than said rice plant, for example, *Echinocloa oryzicola*, or wild *Oryza* species, *Oryza officinalis, Oryza eichingeri, Oryza brachyantha, Oryza perrieri*, etc., mature seeds, or leaf sheaths or roots of a seedling grown under aseptic conditions may be placed on MS agar medium and cultivated. The resulting callus may be subjected to shake culture in a liquid medium under similar conditions as above mentioned.

Each of the thus cultured cells is treated with a cell wall degrading enzyme such as cellulase, macerozyme or the like in an enzymic solution containing the enzymes at 25–30° C. and 0–50 spm (stroke per minute) for about 3–16 hours to prepare corresponding protoplasts from each of said cultured cells. After the enzyme treatment, filtration may be effected to remove undigested materials, and KMC solution (0.118 M KCl, 0.0817 M $MgCl_2$ and 0.085 M $CaCl_2$, pH 6.0: see Theor. Appl. Genet., 53, 57–63 (1978)), may be added to the filtrate in an amount of 2 to 5 times by volume of the filtrate. The resulting mixture may be centrifuged to produce purified protoplasts.

The resulting protoplasts are suspended in a solution containing mannitol, morpholinoethanesulphonic acid (MES), etc., and then subjected to cell fusion by, for example, electric treatment with alternate and direct currents.

It is preferred to preliminarily treat the protoplasts from rice (*Oryza sativa*) with an iodine compound, such as iodoacetamide, monoiodoacetic acid or the like, of a concentration of 1–50 mM near 4° C. for 5–30 minutes.

On the other hand, the protoplasts from another gramineous plant may optionally be subjected to preliminary treatment with a Rhodamine compound, such as Rhodamine 6G or the like, of a concentration of 5–100 $\mu$M at room temperature for about 10–120 minutes. In such treatment, the density of the protoplast may preferably be $1 \times 10^5$ to $1 \times 10^7$ cells per ml. Such treatment renders the protoplasts incapable of dividing by themselves in a culture medium for cultivating fused cells as will described hereinbelow. If the protoplast from another gramineous plant other than rice has no capacity of division in the culture medium described below, such treatment as described above with a Rhodamine compound may not necessarily be effected.

In the cell fusion of the protoplasts by electric treatment, both the protoplasts from rice and the protoplasts from another gramineous plant are mixed in a solution containing 0.2–0.6 M mannitol and 0.05–0.5% MES so that the cell densities of the two protoplasts are equal to each other and the total cell density is $1-3 \times 10^7$ per ml; an alternate current of 2,000–7,000 kHz and 50–500 V/cm is applied to the mixture for 1 to 30 seconds; 1 to 10 pulses of direct current with 1.5–7.5 KV/cm are then applied with a direction of each pulse of 1–100 microseconds at an interval between two successive pulses of 0.1 to 5 seconds; and thereafter, the above mentioned alternate current is again applied for 1 to 200 seconds.

Preferably, the thus treated cells may be suspended in e.g. R2/MS liquid medium containing the inorganic components of R2 and the vitamins of MS, or MS medium, preferably containing 0.2–0.5% potassium nitrate as a nitrogen source; the suspension may then be mixed with an equal amount of R2/MS medium or MS medium containing about 1.0–3.0% agarose; and the resulting mixture may be quickly spread in a petri dish to solidify it into a thin gel film. The cell density in the gel may be about $2-8 \times 10^6$ per ml and the thickness of the agarose film may preferably be approximately 0.7 mm on the average.

The solidified agarose gel may then be cut into pieces having a size of about 5 to 20 mm and cultivated in the aforementioned liquid culture medium. This cultivation may be effected under the dark at 23–27° C. with slow shaking (20–50 rpm) in the presence of cultured cells of rice plant (Oryza sativa) in an amount of about 100–300 mg per fresh weight per petri dish.

Alternatively, such cultured cells of rice may be placed in a vessel equipped with a membrane filter or the like at the bottom. This vessel may be immersed into the liquid medium containing the above treated cells to allow the exchange of nutrients through the filter.

Preferably, the cultured cells of rice used in the invention may essentially consist of small cell aggregates showing active cell division. Such cultured cells may be easily obtained according to known methods: for example, a callus obtained from a seed, stem, root or anther of rice plant may be sub-cultured in a liquid medium to select desirable cells.

During such culture of the agarose gel as described above, only the properly fused cells can proliferate.

After 3 to 7 day culture the first cell division will be observed, and by about 10th day, all the cells having the division capacity will have finished their first cell division. These cells can now proliferate without co-existence of cultured rice cells. Then, the culture medium is replaced with a new medium while at the same time the cultured rice cells are removed out. In 3 to 5 week culture colonies of about 0.5 to 1.0 mm in diameter will be formed.

These colonies are then cultivated in a growth medium, for example, an agar medium comprising $N_6$ basal medium (Sci. Sin., 16, 659–688 (1975)) to which about 2 mg/l of a plant hormone, e.g., 2,4-dichlorophenoxyacetic acid (2,4-D) and 0.1–1.0% agarose are added, under light of 1,000–4,000 lux at 23–27° C. for 2 to 4 weeks. Thus, a hybrid callus of 3 to 6 mm in diameter is produced.

The hybrid callus is cultivated in, e.g., $N_6$ medium containing 0.5–1.5% agarose, which is hormone-free or contains 1–10 mg/l cytokinin, under 2,00014 4,000 lux at 23–27° C. The formation of somatic embryo will be observed in 2 to 10 weeks. Further cultivation in a hormone-free $N_6$ medium or the like for additional 2 to 3 weeks will give transplantable hybrid plants.

DESCRIPTION OF THE PREFERRED EMBODIMENTS

The present invention will be more fully described by the following examples. These examples are given by way of illustration only and not intended to limit the scope of the invention defined in attached claims.

EXAMPLE 1

(1) Preparation of Protoplasts

A mature seed of a rice variety (Oryza sativa) NIHONBARE was sterilized, placed on MS agar medium (2 mg/l 2,4-D, 8 g/l Bactoagar, pH 5.8), and cultured for 3 weeks at 26° C. under 3,000 lux to induce a callus. The callus was then cultivated with shaking in R2/MS liquid medium (inorganic salts of R2, vitamins of MS, 1 mg/l 2,4-D, 30 g/l sucrose, pH 5.8) for several weeks at 120 rpm, 25° C. under 3,000 lux. The cultured callus was treated in an enzymic solution containing 4% Cellulase RS, 1% Macerozyme R-10 and 0.4 M mannitol (pH 5.6) at 30° C. for 3 to 4 hours. The enzymatically treated materials were then filtered. Four times by volume, based on the volume of the resulting filtrate, of KMC solution (0.118 M KCl, 0.085 M $CaCl_2$, 0.0817 M $MgCl_2$, pH 6.0) was added to the filtrate. The resulting mixture was centrifuged and the precipitated protoplasts were collected and further washed twice with the KMC solution.

On the other hand, a seed of Echinocloa oryzicola was sterilized and incubated on hormone-free MS medium (30 g/l sucrose, 8 g/l Bactoagar, pH 5.8) at 25° C. under 3,000 lux to induce germination. Ten days later, leaf sheaths of the plant were cut into disks of 0.5 mm in thickness. These disks were placed on the aforementioned agar medium containing 4 mg/l 2,4-D and cultured for 3 weeks at 25° C. under 3,000 lux to induce a callus. The callus was then cultured with shaking in MS liquid medium (1 mg/l 2,4-D, 30 g/l sucrose, pH 5.8) for several weeks at 120 rpm, 25° C. under 3,000 lux. The cultured cells were treated in an enzymic solution containing 4% Cellulase RS, 1% Macerozyme R-10 and 0.4 M mannitol (pH 5.6) at 30° C. for 3 to 4 hours. After filtration of the thus treated materials, four times by volume, based on the volume of the filtrate, of the KMC solution was added to the filtrate. The resulting mixture was centrifuged and the precipitated protoplasts were collected and further washed twice with the KMC solution.

(2) Iodoacetamide Treatment

The protoplasts, $6 \times 10^6$ cells, prepared in (1) above from the cultured cells of the rice variety, were suspended in KMC solution (5 ml). A 50 mM iodoacetamide solution was added to the suspension so that the final concentration was 25 mM and incubated under the dark at 4° C. for 15 minutes. After the treatment, the materials were centrifuged for 5 minutes and the collected protoplasts were twice washed with KMC solution.

(3) Cell Fusion

The protoplasts, prepared from Echinocloa oryzicola and Oryza sativa in (1) and (2) above, respectively, were suspended in a solution containing 0.45 M mannitol and 1 g/l MES (pH 5.6) so that the cell density of each protoplast was $1-2 \times 10^7$ per ml. The suspension (100 to 200 μl) was subjected to electric treatment by GCA1000Z cell fusion apparatus. The fusion was effected by first applying an alternate current of 4,000 KHz, 250 V/cm for 6 to 7 seconds, then a direct current of 3.5 KV/cm for 10 microseconds three times with an interval of 1 second, and again an alternate current of 4,000 KHz while gradually reducing the voltage from 250 V/cm over 30 seconds. The thus fused cells were directly cultivated in the following steps.

(4) Culture of the Fused Cells

The fused cells prepared in (3) above were suspended in R2/MS medium (2 mg/l 2,4-D, 0.4 M sucrose, pH 5.6) containing 0.4% $KNO_3$. This suspension (0.5 ml) was mixed with 0.5 ml of R2/MS medium containing 2% agarose which had been warmed to about 40° C., and the mixture was quickly and uniformly spread on a petri dish of 35 mm in diameter to solidify. The cell density was then $5 \times 10^6$ per ml.

The solidified agarose gel was cut into pieces of about 5 mm $\times$ 20 mm. The pieces were placed on 5 ml of the same R2/MS medium as described above contained in a petri dish of 6 cm in diameter. At the same time, 100 to 150 mg (fresh weight) of cultured cells of rice (*Oryza sativa*) was added to the petri dish.

These cultured rice cells were prepared in the following manner: A callus derived from a root of rice plant in the seedling stage was serially transferred once a week and cultured in a liquid medium. Small cell aggregates of not more than 1 mm in diameter which were present in the thus prepared suspension and showed active cell division were employed as the cultured rice cells.

The cultivation of the fused cells were effected under the dark at 25° C. with slow shaking at about 30 rpm. The first division of these cells started to occur on the 3rd to 5th day of the cultivation and had finished by the 10th day. On the 10th day of cultivation, the cultured rice cells were removed and the agarose gel was transferred to another petri dish containing 5 ml of fresh R2/MS medium. The cultivation was further effected under the same conditions. After 3 to 4 weeks, colonies of 0.5 to 1.0 mm in diameter were formed. The number of colonies formed was approximately 5 to 10 times as large as that attained in the case of conventional cell fusion by PEG-DMSO technique.

These colonies were cultivated in $N_6$ soft agar medium ($N_6$: 2 mg/l 2,4-D, 0.5 mg/l benzylaminopurine, 6% sucrose, 0.25% agarose, pH 5.6) at 25° C. under 3,000 lux for 2 to 3 weeks. Each colony was then transferred to $N_6$ growth medium ($N_6$: 2 mg/l 2,4-D, 0.5 mg/l benzylaminopurine, 6% sucrose, 0.5% agarose, pH 5.6), and further cultivated under the same conditions. A callus of 2 to 3 mm in diameter was formed in 2 to 3 weeks.

This callus was further cultivated in $N_6$ generation medium ($N_6$: 6% sucrose, pH 5.6) under the same conditions. After 2 to 8 weeks there was observed the formation of a somatic embryo. The somatic embryo was further grown by conventional procedures. A plant was thus obtained.

The thus obtained calluses were subjected to the conventional hybrid assay by analyzing the number of chromosomes, karyotypes, electrophoretic patterns of isozymes such as leucine aminopepidase, and morphological characteristics.

At least 50% of the obtained calluses were shown to be hybrid. Four calluses (H1 to H4) had the number of chromosomes as shown in Table 1 below. The electrophoretic patterns of isozymes for H1 and H2 are shown in FIG. 1.

TABLE 1

| Number of Chromosomes of Rice, Echinocloa and Hybrid Calluses | | | | | |
|---|---|---|---|---|---|
| | Oryza sativa | Echinocloa oryzicola | Hybrid callus | | |
| | | | H1 | H2 | H3 | H4 |
| Number of chromosomes | 24 | 36 | 120–130 | 120–130 | about 100 | about 120 |

EXAMPLE 2

In the procedures of Example 1 (1), a seed of *Oryza perrieri* was used instead of the seed of *Echinocloa oryzicola*. The seed was treated for 4 to 5 hours at 45° C., sterilized, placed on MS agar medium (4 mg/l 2,4-D, 8 g/l Bactoagar, pH 5.8), and further treated in a similar manner to that of Example 1 to prepare protoplasts.

Then, the protoplast was fused with the protoplast from a cultivated rice *Oryza sativa* prepared in Example 1 (1) and (2), by the same method as in Example 1 (3).

Figure 2:
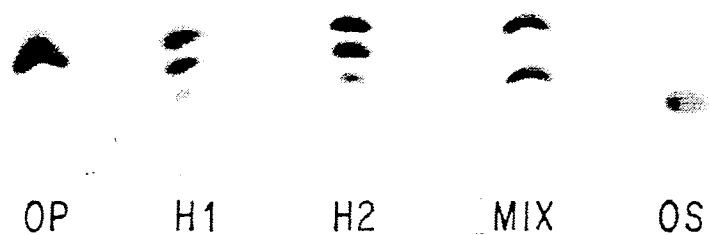
FIG. 2 is a picture showing the electrophoretic band pattern of ADH (alcohol dehydrogenase) isozymes; OS corresponds to rice (*Oryza sativa*), OP to *Oryza perrieri*, $H_1$ and $H_2$ to hybrid plants obtained according to the process of the invention, and MIX to a mixture of OS and OP.

The resulting fused cells were cultivated as in Example 1 (4) to produce plants H1 and H2. The electrophoretic results of their alcohol dehydrogenase (ADH) isozymes are shown in FIG. 2.

In the same procedures as in Example 1 (4), H1 and H2 were allowed to re-differentiate and then to grow to give a plant. Hybrid assay was performed based on the number of chromosomes, electrophoretic pattern of isozymes, and morphological characteristics.

Further, hybrid plants between rice (*Oryza sativa*) and *Oryza officinalis, Oryza eichingeri,* or *Oryza brachyantha* were obtained by similar procedures.

As seen from the above examples, gramineous hybrid plants which cannot be obtained the conventional breeding methods may be prepared with a high reproducibility and a high efficiency according to the present invention.

What is claimed is:

1. A process for preparing a gramineous hybrid plant, comprising:
   a) preparing a first protoplast from a callus or suspension cell derived from *Oryza sativa,*
   b) preparing a second protoplast from a callus or suspension cell derived from plant *Oryza eichingeri,*
   c) subjecting the first protoplast to treatment with an iodine compound, comprising iodoacetamide or monoiodoacetic acid,
   d) subjecting the second protoplast to treatment with a Rhodamine compound, comprising Rhodamine 6G,
   e) subjecting the protoplast to cell fusion by successive electric treatment with (i) an alternate current of 2,000–7,000 KHz and 50–500 V/cm for 1 to 30 seconds, with (ii) 1 to 10 pulses of direct current with 1.5–7.5 KV/cm, the duration of each pulse being 1–100 microseconds at an interval between two successive pulses of 0.1 to 5 seconds, and then with (iii) said alternate current for 1 to 200 seconds,
   f) co-cultivating the fused cells under dark at 23–27° C. with slow shaking of 20–50 rpm in a culture medium containing cultured cells of *Oryza sativa* as nurse cells in an amount of about 100–300 mg per fresh weight per petri dish, using 0.2 to 0.5% potassium nitrate as a nitrogen source to from colonies, and g) further cultivating the formed colonies in a culture medium containing a plant hormone.

2. The process according to claim 1, wherein said cell fusion of said protoplast comprises mixing said protoplast in a solution containing 0.2-0.6 M mannitol and 0.05-0.5% MES so that the cell densities of the protoplast are equal to each other, the cell density being $1 \times 10^7$ to $3 \times 10^7$ per ml.

3. The process according to claim 1, wherein the plant hormone is 2,4-dichlorophenoxyacetic acid.

4. The process according to claim 1, wherein protoplast is treated with said iodine compound for about 5-30 minutes using a concentration of said iodine compound of about 1-50 mM.

5. The process according to claim 1, wherein said protoplast is treated with said Rhodamine compound for about 10-120 minutes using a concentration of said rhodamine compound of about 5-100 $\mu M$.

6. The process according to claim 1, wherein a protoplast density in the range of $1 \times 10^5$ to $1 \times 10^7$ cells per ml is used.

* * * * *

UNITED STATES PATENT AND TRADEMARK OFFICE
CERTIFICATE OF CORRECTION

PATENT NO. : 5,250,433
DATED : October 5, 1993
INVENTOR(S) : Ko Shimamoto et al.

It is certified that error appears in the above-indentified patent and that said Letters Patent is hereby corrected as shown below:

On the title page, Item [22],

The filing date, should read: --Oct. 4, 1991--

Signed and Sealed this

Fifth Day of April, 1994

Attest:

BRUCE LEHMAN

Attesting Officer     Commissioner of Patents and Trademarks